United States Patent [19]

Sneider

[11] 4,223,814

[45] Sep. 23, 1980

[54] EXPANDABLE SYRINGE AND SPRINKLER CAP THEREFOR

[76] Inventor: Vincent R. Sneider, 3422 Hallcrest Dr. N.E., Atlanta, Ga. 30319

[21] Appl. No.: 12,255

[22] Filed: Feb. 15, 1979

Related U.S. Application Data

[62] Division of Ser. No. 756,237, Jan. 3, 1977, Pat. No. 4,168,032.

[51] Int. Cl.³ .............................................. B65D 47/08
[52] U.S. Cl. .................................... 222/565; 220/281; 239/327
[58] Field of Search ................ 239/327, 374; 222/565, 222/505, 151, 563; 220/281; 215/301

[56] References Cited

U.S. PATENT DOCUMENTS

| | | | |
|---|---|---|---|
| 3,419,198 | 12/1968 | Pettersen | 222/563 |
| 4,068,663 | 1/1978 | D'alessandro | 128/232 X |

FOREIGN PATENT DOCUMENTS 589097  1/1924  France ..................................... 222/151

*Primary Examiner*—Bruce H. Stoner, Jr.
*Assistant Examiner*—Gene A. Church
*Attorney, Agent, or Firm*—Hosier, Niro & Daleiden, Ltd.

[57] ABSTRACT

An expandable syringe comprising a bag having an opening through which liquid may pass. A closed end tubular view stem projects outwardly from the bag opening and has an orifice in the side thereof in fluid communication with the interior of the bag. A nozzle has a female coupler sized to be movably mounted about the valve stem. The nozzle coupler has a valve seat against which the valve stem closed end may operationally engage in controlling the flow of liquid between the bag and nozzle. The bag may comprise a corrugated container or a shell having first and second openings and flexible pocket mounted to the shell sealing the first opening and sized for maneveur into and out of the shell through the first opening to displace liquid out of the shell. A nozzle or sprinkler cap may be detachably mounted to the shell over the second opening. Upon detachment of the nozzle or cap from the shell liquid may be introduced into the shell through the second opening thereby forcing the pocket to a position outside the shell. The nozzle or sprinkler cap may then be attached and the pocket squeezed into the shell thereby forcing the liquid out of the shell and nozzle. The sprinkler cap comprises a tubular member and an apertured sprinkler plate mounted therein having an elongated plate ledge. An articulated cover is joined to the tubular member at a joint aside the sprinkler plate. The cover has two sections hinged together along an elongated hinge parallel the plate ledge between the ledge and corner joint.

6 Claims, 16 Drawing Figures

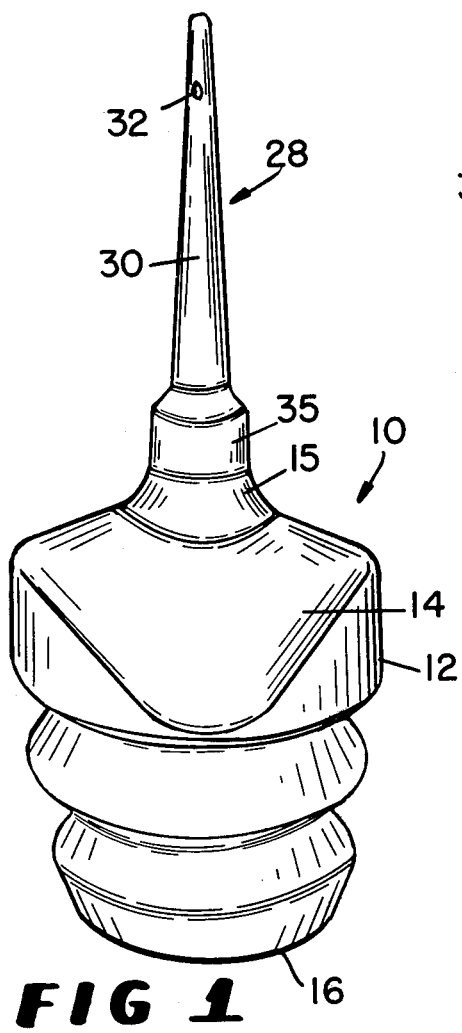
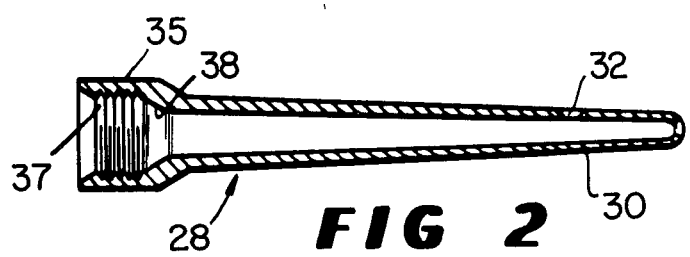
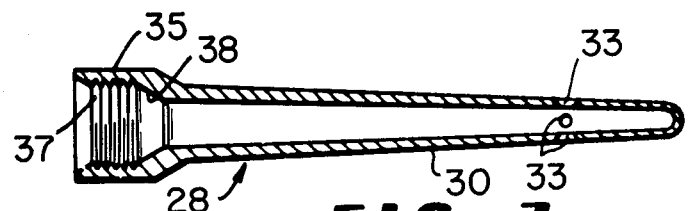
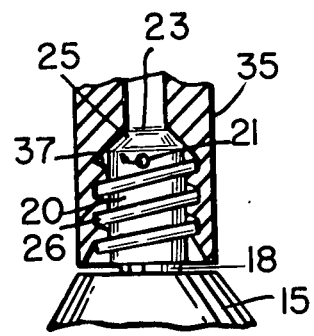
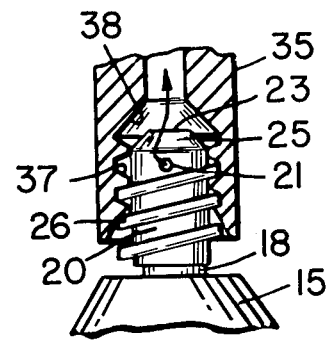
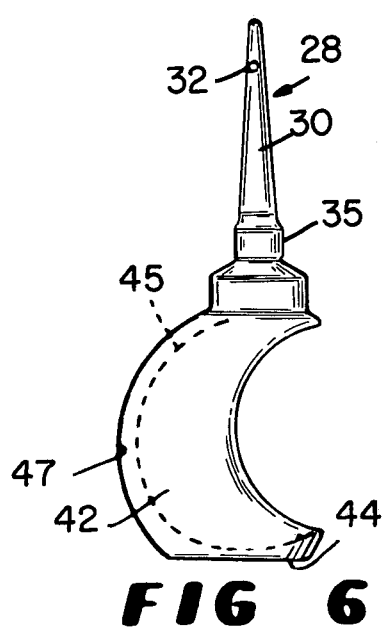
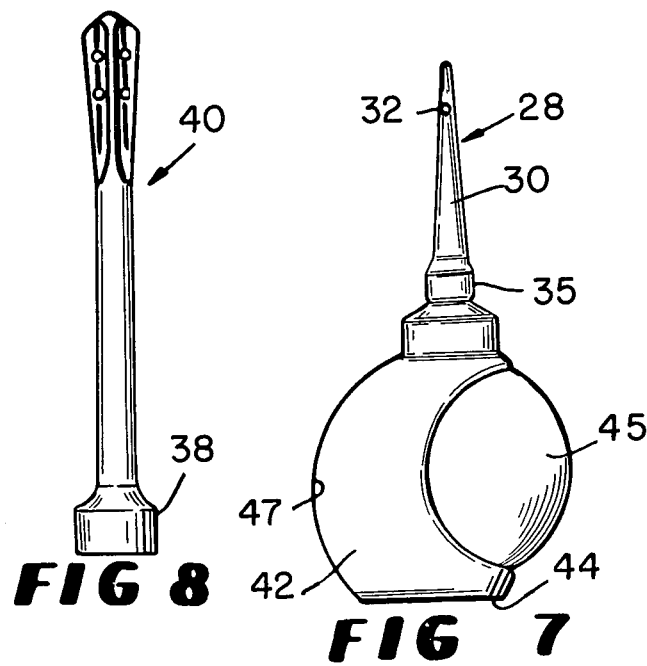
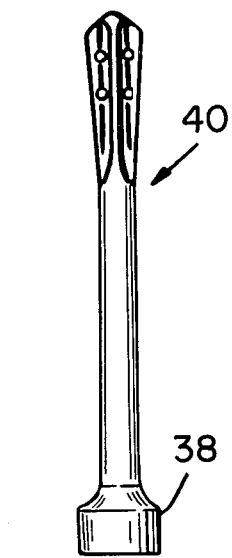

EXPANDABLE SYRINGE AND SPRINKLER CAP THEREFOR

This is a divisional application of application Ser. No. 756,237, filed Jan. 3, 1977, now U.S. Pat. No. 4,168,032.

BACKGROUND OF THE INVENTION

This invention relates generally to expandable syringes and to sprinkler caps which may be used therewith.

Vaginal douche devices, and particularly vaginal syringes are well known in the art and in commerce. One general form of syringe includes a substantially flat bag which may be expanded by filling with water or other appropriate liquid. After the liquid has been placed in the bag, a nozzle is inserted into the filling spout of the bag so that the apparatus may be used as a syringe. The expanded bag may be depressed to assist in urging the liquid from the bag, and through the nozzle. One particular syringe of this general description is known as the "Shy" douche device.

While syringes of the above described general type have been used for some considerable length of time and have achieved some commercial success, there are several problems inherent in the design of this type of prior art syringe. Generally, once the nozzle is inserted into the syringe, there is no means for controlling the flow of liquid from the syringe and through the nozzle. When there is pressure because of the introduction of a quantity of liquid under pressure into the syringe, it is possible to inadvertently dispense the liquid upon insertion of the nozzle into the syringe. The flat bags have also been difficult to manipulate in completely expelling liquid and in filling operations. With some syringes, sprinkler caps are used as in flushing exterior skin areas. Those sprinkler caps which have included covers permanently secured to the cap have not operated well. Typically, they have been formed of resilient materials such as soft plastics which have orientation memory. That is to say that they have tended to return to one position once flexed to another whereupon the user must manually hold or fasten the cover in its tensed position.

Accordingly, it is a general object of the present invention to provide an improved expandable syringe.

It is another general object of the invention to provide an improved sprinkler cap for a receptacle such as an expandable syringe.

More specifically, it is an object of the invention to provide an expandable syringe with valve means for controlling the flow of liquid between the syringe bag and nozzle.

Another object of the invention is to provide an expandable syringe with valve means of the type described that is simple to construct and operate.

Another object of the invention is to provide an expandable syringe with an improved expandable bag.

Another object of the invention is to provide an expandable bag for a syringe that may be easily filled with liquid and from which liquid may be easily expelled.

Yet another object of the invention is to provide an improved sprinkler cap for an expandable syringe or receptacle.

Still another object of the invention is to provide a sprinkler cap of the type first described with a permanently attached cover that may be positioned in both closed and open positions without spring back tendency, and which is also simple and economic in construction and easy to operate.

SUMMARY OF THE INVENTION

In one form of the invention an expandable corrugated syringe is provided comprising a bag having an opening through which liquid may pass. A closed end tubular valve stem projects outwardly from the bag opening which stem has one or more orifices in the side thereof in fluid communication with the interior of the bag. A nozzle is provided having a female coupler on an end thereof sized to be movably mounted about the valve stem. The coupler has a valve seat against which the valve stem closed end may operationally engage in controlling the flow of liquid between the bag and nozzle.

In another form of the invention an expandable syringe is provided comprising a shell having first and second openings. A flexible pocket is mounted to the shell sealing the first opening which pocket is sized for movement into and out of the shell through the first opening. A nozzle is detachably mounted to the shell over the second opening. So constructed, the nozzle may be detached from the shell and liquid introducted into the shell through the second opening thereby forcing the pocket to a position outside the shell, and the nozzle attached and the pocket squeezed into the shell thereby expelling the liquid out of the shell and nozzle.

In yet another form of the invention a sealable sprinkler cap is provided comprising a tubular member adapted to be mounted to a receptacle outlet. An apertured sprinkler plate is mounted within the tubular member having an elongated plate ledge extending between opposed interior surfaces of the tubular member. An articulated cover is joined to the tubular member at a joint aside the sprinkler plate which cover has two sections hinged together along an elongated hinge parallel the plate ledge between the ledge and cover joint.

BRIEF DESCRIPTION OF THE DRAWING

FIG. 1 is a perspective view of an expandable syringe incorporating principles of the invention in one preferred form.

FIG. 2 is a longitudinal cross-sectional view of the nozzle component of the syringe shown in FIG. 1.

FIG. 3 is a longitudinal cross-sectional view of a modified version of the nozzle shown in FIG. 2.

FIGS. 4 and 5 are side elevational views of the valve stem component of the syringe shown in FIG. 1 together with the nozzle coupler component shown in cross section attached therein in valve closed and valve opened positions, respectively.

FIGS. 6 and 7 are side elevational views of an expandable syringe embodying principles of the invention in an alternative form with the syringe shown in evacuated and filled positions, respectively.

FIG. 8 is a side elevational view of another nozzle which may be substituted for the nozzle illustrated on the syringes shown in FIGS. 1 and 6.

DESCRIPTION OF THE PREFERRED EMBODIMENT

Figure 9:
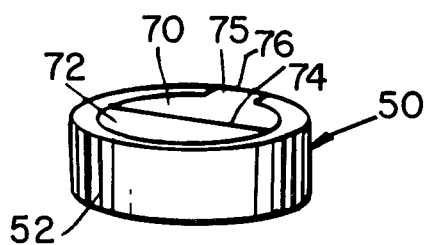
FIG. 9 is a perspective view of a sprinkler cap shown in a closed position embodying principles of the invention in another form which cap may be used with the syringes shown in FIGS. 1 and 6.

Referring now in more detail to the drawings, there is shown in FIG. 1 an expandable syringe 10 having an expandable bag 12 in the form of a bellows. The upper surface of the bellows-shaped bag is convex and provided with two opposed gripping surfaces 14 about a tubular bellour neck 15. The bottom 16 of the bag is flat thereby enabling it to be set erect upon a supporting surface. An open-ended, tubular throat or spout 18 projects out of the bag neck about which is threadedly mounted a tubular, closed end valve stem 20 having an orifice 21 positioned beyond the open end of throat 18 in fluid communication with the interior of bag 12. The exterior surface of the closed end of the valve stem consists of a circular planar section 33 from which a truncated conical section or apron 25 depends. Helical screw threads 26 are formed about the exterior side of the valve stem which terminate aside orifice 21.

A nozzle 28 is seen to be mounted to the bag in FIG. 1. As most clearly shown in FIG. 2, the nozzle is designed for enema usage and includes a tapered, tubular section 30 having a port 32 in the side thereof. With the modified version shown in FIG. 3 four, mutually spaced, coplanar ports 33 are provided. The nozzle has a female connector 35 at an open end thereof. The female connector has internal helical screw threads 37 and a frusto-conical valve seat 38. This connector may also be constructed on a vaginal douche nozzle such as on the nozzle 40 shown in FIG. 8 which otherwise may be of conventional construction.

In operation syringe 10, which is prepacked with dry chemical agents, is filled with liquid such as water by temporarily unscrewing the nozzle and valve stem from the bag throat and introducing water into the expandable bag 12 through the open ended throat 18. The valve stem is then screwed back on the bag throat and nozzle 28 screwed down on the valve stem until the truncated conical surface 25 of the stem end abuts the valve seat 38 of the nozzle coupler. This constitutes the valve closed position shown in FIG. 4. In this closed position any liquid which may be emitted out of stem orifice 21 is trapped thereabout between the valve and screw threads. The syringe is then shaken to mix the chemicals in the flooded bag. The nozzle may then be longitudinally inserted into a human cavity to be treated or cleansed so that gripping surfaces 14 fit snuggly against the human body. Once in place the nozzle may be rotated slightly thereby moving the concical surface of the closed stem end away from the valve seat surface of the coupler, and bag 10 then be collapsed to evacuate the contents of the bag through the nozzle. The liquid solution thereupon flows out of the bag through the valve stem orifice and up through the nozzle finally to be discharged out of ports 32 or 33. As the nozzle coupler remains threadedly mounted upon the valve stem, the liquid is inhibited by the mating screw threads from escaping out between the nozzle and bag throat. Upon depletion of the liquid the nozzle is removed from the human orifice and the syringe discarded or reused if desired. The bellows arrangement of the bag permits evacuation of substantially all of the contents of the bag upon collapse of the bag.

With reference next to FIGS. 6 and 7, an expandable syringe having the nozzle and valve means of the construction first described is shown. Here, however, the syringe bag is of different construction and is seen to comprise a relatively stiff shell having a small opening in the top thereof into which liquid may be introduced, and a large opening in the side thereof. The shell, which is partially spherical, has a flat bottom 44 which renders it capable of being set upon a flat supporting surface. A flexible pocket or bulb is secured about the interior surface of the shell which defines the large shell opening thereby sealing the opening and rendering the shell watertight. The pocket or bulb is shaped and sized so as to conform closely to that of the interior surface of the shell, as shown in FIG. 6, when fully depressed into the shell, and to render the shell and pocket combination generally sperically as shown in FIG. 7 when fully distended out of the shell opening, except for the shell bottom and top.

In operation, liquid may be poured through the top opening in the shell to fill the syringe bag. As the bag is filled the pressure of the liquid forces the pocket out of the shell opening. This action is also assisted by direct contact with the descending water impinging upon the pocket when the pocket is disposed within the shell beneath the shell opening. Once completely filled the syringe may be operated as previously described except that here the relatively stiff shell is gripped and finger pressure applied to the pocket in forcing the stored liquid out of the syringe nozzle. Pressure is continuously applied until the pocket engages the interior surface 47 of the shell opposite the side opening. Finger pressure may then be applied with a wave like action in expelling most of the remaining liquid out of the syringe. The syringe may then be discarded or cleansed and compactly stored upright in the position shown in FIG. 6.

With reference next to FIGS. 9–16, a sealable sprinkler cap 60 of hard plastic construction is shown releasably secured to a syringe in lieu of a nozzle of the type just described having a shell 42 and a flexible pocket 45. The sprinkler cap is seen to include a cylindrical, tubular member 52 having an inwardly extending annular lip 54 at its lower end adapted to be snapped upon or threaded onto (threads are not shown) an unshown mating tubular neck extension of shell 42. A sprinkler plate 56 in the form of a semi-circular disc is mounted within the tubular member along a plane oriented radially of the tubular member axis. The sprinkler plate is provided with a set of apertures 58 and has an elongated ledge 60 extending between opposed portions of the tubular member interior wall 62. Another generally semi-circular plate 64 is mounted within the tubular member along another plane oriented substantially radially of the tubular member axis that is axially offset from the plane of the sprinkler plate. The two plane are joined together beneath ledge 60 by a rib 65. Plate 64 is flared upwardly at section 66 adjacent its juncture with wall 62.

With continued reference to FIGS. 9-16, the sprinkler cap is further seen to be provided with an articulated cover having two generally semi-circular sections 70 and 72 hinged together along an elongated hinge 74 of reduced thickness aside and parallel to ledge 60. Cover section 70 has a unitary leg extension 75 that is itself hinged to an upper, arcuate end portion 76 of the tubular member. Cover section 72 is provided with a set of resilient plugs 78 which depend from the lower surface thereof in alignment with the set of apertures 58 in sprinkler plate 56.

Figure 10:
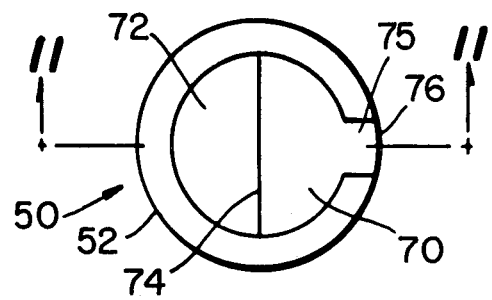
FIG. 10 is a plan view of the cap shown in FIG. 9.
Figure 11:
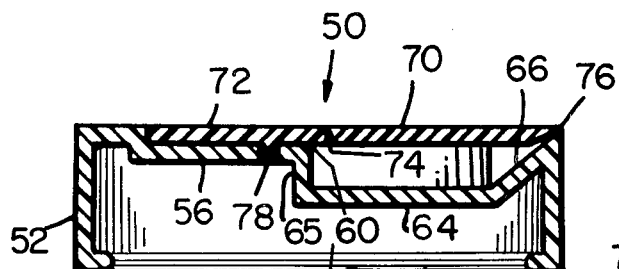
FIG. 11 is a cross-sectional view of the cap shown in FIG. 10 taken along plane 11—11.
Figure 13:
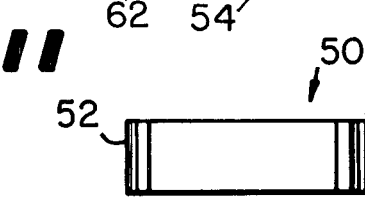
FIG. 13 is a side elevational view of the cap shown in FIG. 12.
Figure 12:
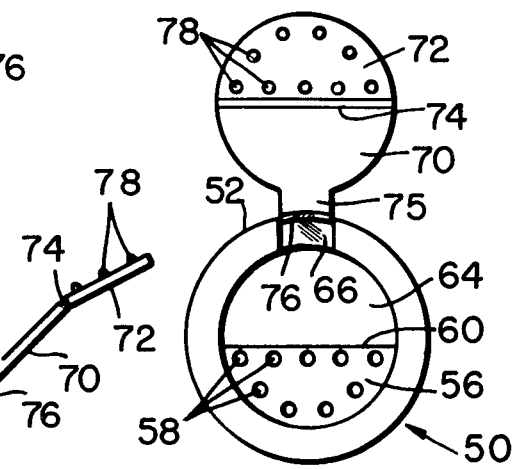
FIG. 12 is a plan view of the cap shown in FIG. 9 in an open position.
Figure 14:
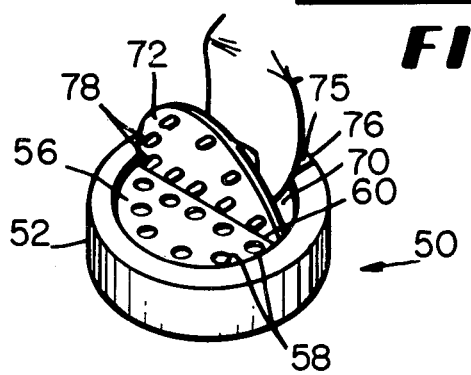
FIG. 14 is a perspective view of the cap shown in FIG. 9 shown together with a human thumb urging the cap to an open position.
Figure 15:
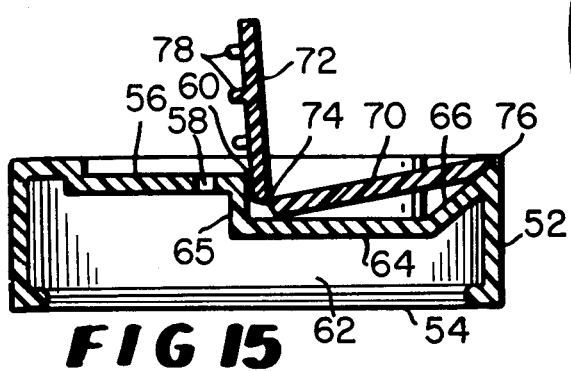
FIG. 15 is a cross-sectional view of the cap shown in FIG. 9 in an open position.
Figure 16:
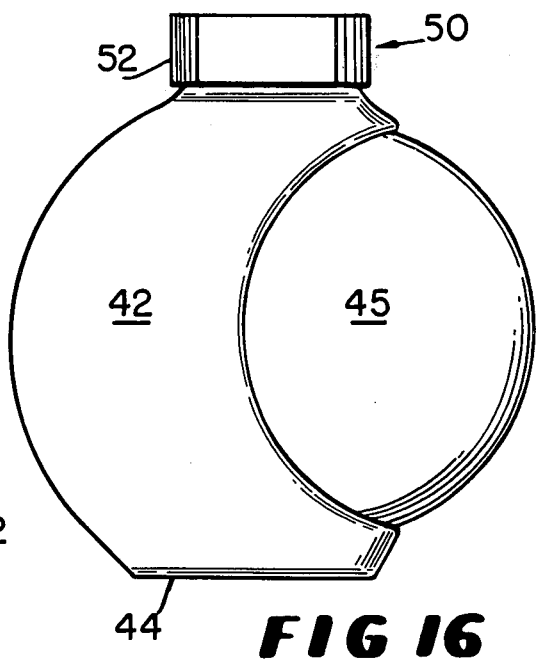
FIG. 16 is a side elevational view of the expandable syringe shown in FIGS. 6 and 7 with the cap shown in FIG. 9 substituted for the syringe nozzle.

So constructed, the two cover sections 70 and 72 may be moved to the mutually planar position shown in FIGS. 9-11 with plugs 78 seated within apertures 58 thereby sealing the upper opening of syringe 50. The cap may be opened by manually depressing cover section 70 down against plate 64, as shown in FIGS. 14 and 15, whereupon ledge 60 forces cover section 72 upwardly removing plugs 78 from apertures 58 and swinging section 72 out from over the sprinkler plate 56. The syringe may now be collapsed to spray liquid out of the cap or inverted enabling liquid therewithin to gravitate out through the sprinkler plate. During this operation there is little tendency for the articulated cover to resume its closed or a semi-closed position since its hinge area is wedged aside and beneath ledge 60. The cover may later be returned to its closed position by simply pressing down cover section 72 whereupon plugs 78 reenter apertures 58 thereby simultaneously creating a liquid-tight seal and holding the cover firmly in its closed position.

It should be understood that the first described embodiments merely illustrate principles of the invention in selected preferred forms. Many modifications, additions and deletions may, of course, be made thereto without departure from the spirit and scope of the invention as set forth in the following claims.

I claim:

1. A sealable sprinkler cap for a receptacle comprising a tubular member adapted to be mounted to a receptacle outlet; a sprinkler plate mounted within said tubular member and having a plurality of apertures therethrough, said sprinkler plate having an elongated plate ledge defining a fulcrum extending between opposed interior surfaces of said tubular member; and an articulated cover joined to said tubular member at a joint aside said sprinkler plate and having two cover sections hinged together along an elongated hinge parallel said plate ledge between said plate ledge and said cover joint, a plurality of plugs depending from one of said cover sections and insertable into said apertures, and said elongated hinge being located sufficiently close to the fulcrum defined by said plate ledge to provide a mechanical advantage whereby slight depression of the other of said cover sections causes said plugs to be completely withdrawn from said apertures as said one cover section pivots about said fulcrum.

2. A sealable sprinkler cap in accordance with claim 1 wherein said tubular member is cylindrical and said cover hinge extends along a chord of said cylindrical tubular member.

3. A sealable sprinkler cap in accordance with claim 1 further comprising a second plate mounted within said tubular member joined with said apertured sprinkler plate beneath said plate ledge.

4. A sealable sprinkler cap in accordance with claim 1 in combination with an expandable syringe type receptacle.

5. A sealable sprinkler cap in accordance with claim 4 wherein said expandable syringe comprises a shell having first and second openings and a flexible pocket mounted to said shell sealing said first opening and sized for movement into and out of said shell through said first opening.

6. A sealable sprinkler cap in accordance with claim 5 wherein said cap is mounted about said expandable syringe second opening.

* * * * *

UNITED STATES PATENT AND TRADEMARK OFFICE
CERTIFICATE OF CORRECTION

PATENT NO. : 4,223,814
DATED : September 23, 1980
INVENTOR(S) : Vincent R. Sneider It is certified that error appears in the above—identified patent and that said Letters Patent is hereby corrected as shown below:

Page 1, in the "Abstract", column 2, line 2, after "tubular" delete "view" and insert -- valve --.

In the Description Of The Preferred Embodiment, column 4, line 48, after "cap" delete "60" and insert -- 50 --.

Signed and Sealed this

Sixth Day of January 1981

[SEAL]

Attest:

SIDNEY A. DIAMOND

Attesting Officer

Commissioner of Patents and Trademarks